United States Patent [19]
Faries, Jr. et al.

[11] Patent Number: 5,333,326
[45] Date of Patent: Aug. 2, 1994

[54] METHOD AND APPARATUS FOR PRODUCING SURGICAL SLUSH AND HEATED STERILE LIQUID

[75] Inventors: Durward I. Faries, Jr., McLean, Va.; Bruce R. Heymann, Silver Spring, Md.

[73] Assignee: O. R. Solutions, Inc., Reston, Va.

[21] Appl. No.: 33,639

[22] Filed: Mar. 16, 1993

[51] Int. Cl.$^5$ .................................................. F24J 1/00
[52] U.S. Cl. ........................................ 4/639; 604/113
[58] Field of Search ........................ 4/639; 604/113; 607/113; 62/66

[56] References Cited

U.S. PATENT DOCUMENTS

| | | |
|---|---|---|
| 4,393,659 | 7/1983 | Keyes et al. |
| 4,782,835 | 11/1988 | Bernadini ............ 607/114 |
| 4,934,152 | 6/1990 | Templeton . |
| 5,042,455 | 8/1991 | Yue et al. ............ 607/114 X |
| 5,163,299 | 11/1992 | Faries, Jr. et al. . |

Primary Examiner—John C. Fox

[57] ABSTRACT

The features of a surgical slush machine are augmented by a separate warming basin for surgical liquid to thereby permit simultaneous availability of the warmed liquid and surgical slush. The slush cooling basin is disposed adjacent the warming basin, and a common sterile drape is disposed over and contoured to both basins to provide separate sterile receptacles in the drape for the liquid and slush. Basin centering indicia on the drape facilitate deployment of the drape relative to the basins. Cooling and heating of the respective basins are effected independently with individual power controls.

7 Claims, 3 Drawing Sheets

METHOD AND APPARATUS FOR PRODUCING SURGICAL SLUSH AND HEATED STERILE LIQUID

BACKGROUND OF THE INVENTION

1. Technical Field

The present invention pertains to improvements in methods and apparatus for producing surgical sterile slush. In particular, the invention is an improvement of the methods and apparatus disclosed in U.S. Pat. Nos. 4,393,659 (Keyes et al) and 4,934,152 (Templeton). The disclosures in those patents are expressly incorporated herein in their entireties by this reference.

2. Discussion of the Prior Art

The Keyes et al patent discloses a surgical slush producing system having a cabinet with a heat transfer basin at its top surface. A refrigeration mechanism in the cabinet takes the form of a closed refrigeration loop including: an evaporator in heat exchange relation to the exterior of the heat transfer basin; a compressor; a condenser; and a refrigeration expansion control, all located within the cabinet. A separate product basin is configured to be removably received in the heat transfer basin. Spacers, in the form of short cylindrical stubs or buttons are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile sheet of material, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency in the product basin.

As noted in the Templeton patent, the above-described system has a number of disadvantages. In particular, the separate product basin must be removed and re-sterilized after each use. Additionally, the glycol or other thermal transfer medium is typically highly flammable or toxic and, in any event, complicates the procedure. The Templeton patent discloses a solution to these problems by constructing an entirely new apparatus whereby the product basin is eliminated in favor of a sterilized drape impervious to the sterile surgical liquid, the drape being made to conform to the basin and directly receive the sterile liquid. Congealed liquid is scrapped off the sides of the conformed drape receptacle to form the desired slush.

In addition, Templeton also provides an electrical heater disposed at the bottom of the basin to convert the sterile slush to warmed liquid, or to heat additional sterile liquid added to the basin. Templeton describes the need for such warmed sterile liquid as occurring after a surgical procedure is completed to facilitate raising the body cavity of the surgery patient back to its normal temperature by contact with the warmed liquid. However, there are a number of instances during a surgical procedure when it is desirable to have simultaneous access to both the sterile warmed liquid and the sterile surgical slush. For example, if the surgical slush is not at the desired consistency (e.g., too thick), the availability of warmed sterile liquid to be added to the slush permits rapid adjustability of the slush consistency. Likewise, maintaining instruments at or near body temperature during surgery is a desirable feature permitted by warmed sterile liquid. Of course, if the warmed sterile liquid is simultaneously available with the surgical slush, there is no need to wait for the slush to melt at the end of the surgical procedure. Finally, the simultaneous provision of slush and warm liquid permits the two to be comprised of different compounds as is sometimes necessary for various surgical procedures.

OBJECTS AND SUMMARY OF THE INVENTION

It is an object of the present invention to provide a method and apparatus for simultaneously providing separate surgical slush and warmed surgical liquid during a surgical procedure.

It is another object of the present invention to provide a sterile drape receptacle arrangement for a unit capable of simultaneously providing sterile surgical slush and sterile heated liquid.

In accordance with the present invention a basin for containing warmed surgical liquid is placed adjacent a surgical slush basin of the type, for example, disclosed in the Templeton patent. The warming basin may be a separate unit secured to the pre-existing surgical slush unit, or it may be constructed as part of an integral cabinet for the warming and cooling basins. Each basin has its own power control and temperature control, preferably located on the top surface of the unit adjacent the corresponding basin. If the warmed liquid needs to be rapidly cooled, slush can be transferred immediately from the cooling basin; likewise, if the slush is too thick, warmed liquid can be immediately transferred from the warming basin.

A large surgical drape covers both of the basins and contains the warmed liquid and the slush in a sterile manner. The drape, thusly serving as two receptacles, is provided with two centering indicia (e.g., colored dots, or the like) positioned to correspond to the centers of the two basins. The drape may thus be easily positioned relative to the two basins during deployment to provide the required sterile protection in the operating room.

The above and still further objects, features and advantages of the present invention will be apparent upon consideration of the following detailed description of the specific embodiments thereof, particularly when taken in conjunction with the accompanying drawings wherein like components are designed by like reference numerals.

DESCRIPTION OF THE PREFERRED EMBODIMENTS

Figure 1:
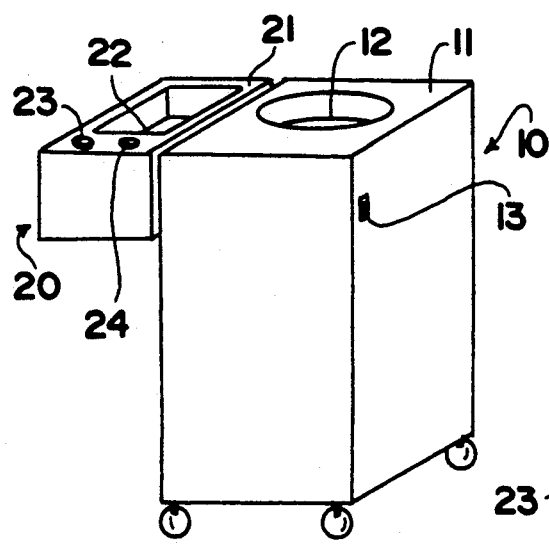
FIG. 1 is a view in perspective of a surgical slush unit and warming unit combination provided in accordance with the present invention.

Referring to FIG. 1 of the accompanying drawings, a surgical slush unit 10 has a heating unit 20 secured thereto. Surgical slush unit 10 may, for example, be configured as the type described and illustrated in the aforementioned Templeton patent, although other configurations are suitable within the scope of the present invention. Surgical slush unit 10 has a top surface 11 with a cooling basin 12 recessed therein. A power switch 13 is disposed on the sidewall of the cabinet in the Templeton unit. In the manner described in the Templeton patent, a suitable sterile liquid, such as a saline solution, is cooled in basin 10 to form surgical slush. In use, the top surface 11 and basin 12 are covered with a sterile liquid impervious drape (not shown in FIG. 1) that can be recessed into the basin. As contemplated by Templeton, ice formed on the sides of the drape is scraped off the drape surface to form slush. In the system described in U.S. Pat. No. 5,163,299 (Faries et al), the formed ice is removed from the drape by gently lifting the drape and shaking it slightly. In either event, surgical slush at the desired consistency may be formed in the receptacle provided by the drape in the cooling basin.

Heating unit 20 may be secured to a sidewall of the cooling unit cabinet such that the top surface 21 of the heating unit is a substantially coplanar extension of the slush unit top surface 11. Attachment of the heating unit 20 to the surgical slush unit cabinet may be by bolts, brackets or other suitable means. A warming basin 22 is recessed into top surface 21. A heater power switch 23 and a temperature controller/indicator 24 are provided on top surface 21 adjacent the warming basin.

Figure 2:
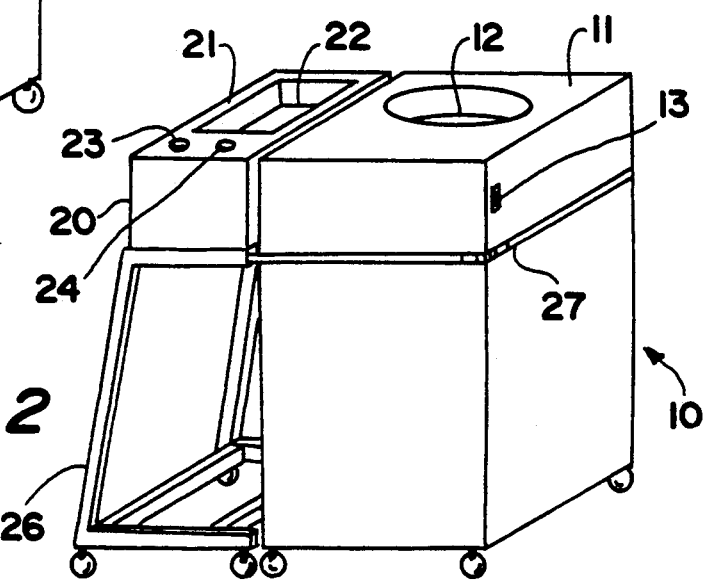
FIG. 2 is a view in perspective of a surgical slush unit and warming unit having a different means for attaching the units together.

Another technique for securing heater unit 20 to pre-existing surgical slush machine 10 is illustrated in FIG. 2. Specifically, a separate wheeled stand 26 has a horizontal support surface for heater unit 20. The thusly supported heater unit has its top surface 21 substantially coplanar with top surface 11 of the surgical slush unit. A belt or strap 27 extends from stand 26 to circumscribe the cabinet of the surgical slush unit 10, thereby preventing inadvertent separation of the slush forming and heating units.

Figure 3:
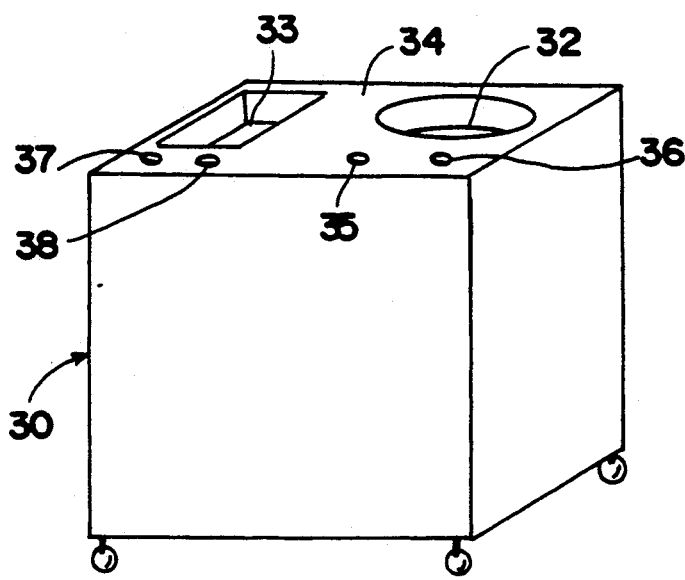
FIG. 3 is a view in perspective of a single unit containing separate heating and cooling basins pursuant to the present invention.

In FIG. 3 there is illustrated an integral assembly 31 wherein a cooling basin 32 for slush and a warming basin 33 for liquid are recessed into the top surface 33 of a common cabinet. Also disposed on top surface 34 are a cooling unit power switch 35, a cooling unit temperature controller/indicator 36, a heater power switch 37 and a heater unit temperature controller/indicator 38.

Figure 4:
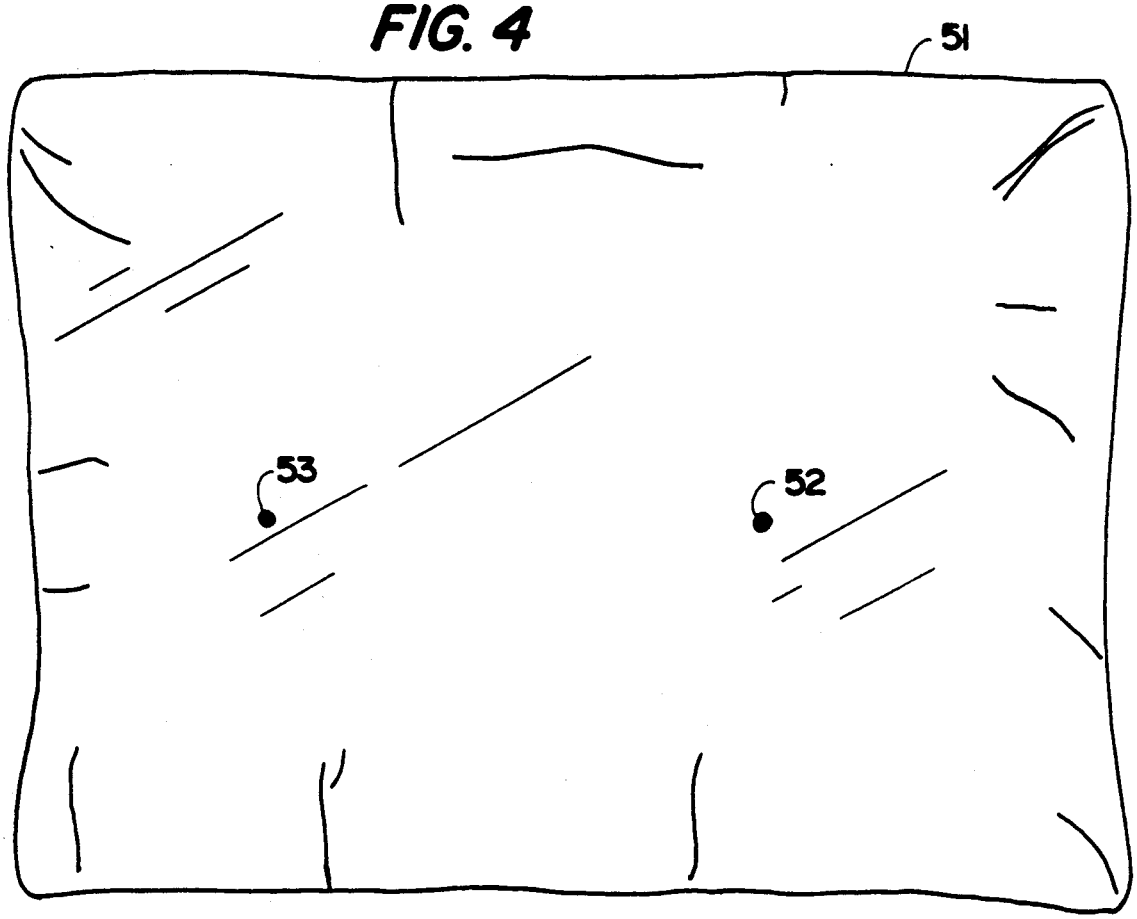
FIG. 4 is a plan view of a surgical drape suitable for use with the embodiments illustrated in FIGS. 1, 2 and 3.

A sterile drape 51 suitable for covering the top surfaces of both the surgical slush unit and heater unit described above (i.e., in FIGS. 1, 2 and 3) is illustrated in FIG. 4. The drape is made of a material that is impervious to the heated liquid and slush, and is sufficiently soft and flexible to conform to the walls of basins 12, 22, 32 and 33. The thickness of the drape is preferably minimized to render thermal transfer therethrough most efficient, yet the thickness is sufficient to resist tearing and puncturing of the drape during whisking of slush and other normal use. Typically, by way of example only, the drape is made of materials commonly used in hospitals for surgical drapes and has a thickness in the range of 4.5 to 6.0 mils. The drape 51 may also be made of polyurethane film as disclosed for the drape in the aforementioned Templeton patent. Such drapes are sufficiently transparent to permit controls 35, 36, 37, 38 to be observed therethrough. Drape 51 is designed to be disposable after a single use and is provided pre-sterilized and pre-packaged in a leak-proof plastic bag or other sealed container to preserve the sterile nature of the drape during storage.

Figure 5:
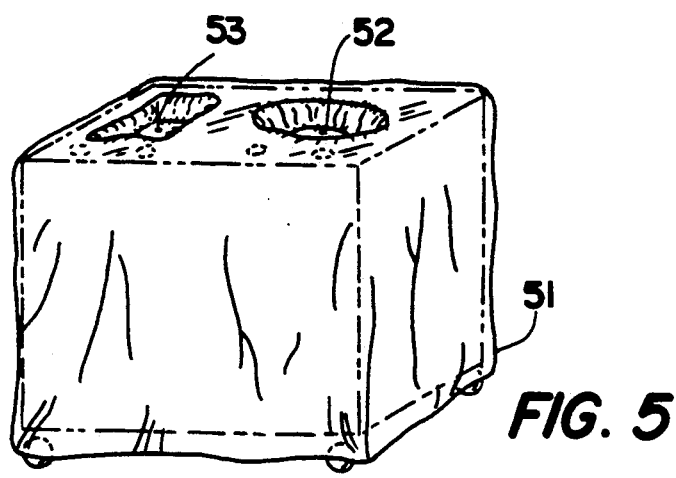
FIG. 5 is a view in perspective showing the surgical drape of FIG. 4 positioned over the unit illustrated in FIG. 3.

An advantageous feature of drape 51 is the provision of two centering marks or indicia 52, 53 adapted to be placed over the centers of the cooling and heating basins, respectively, during installation of the drape. Specifically, the centering indicia are thusly positioned when the drape is pushed down into the two basins until it conforms to the basin shapes. Alternatively, basin-like recesses may be formed in the drape and configured to fit directly into the cooling and heating basins. The installed drape, used in conjunction with the embodiment of FIG. 3, is illustrated in FIG. 5.

Figure 6:
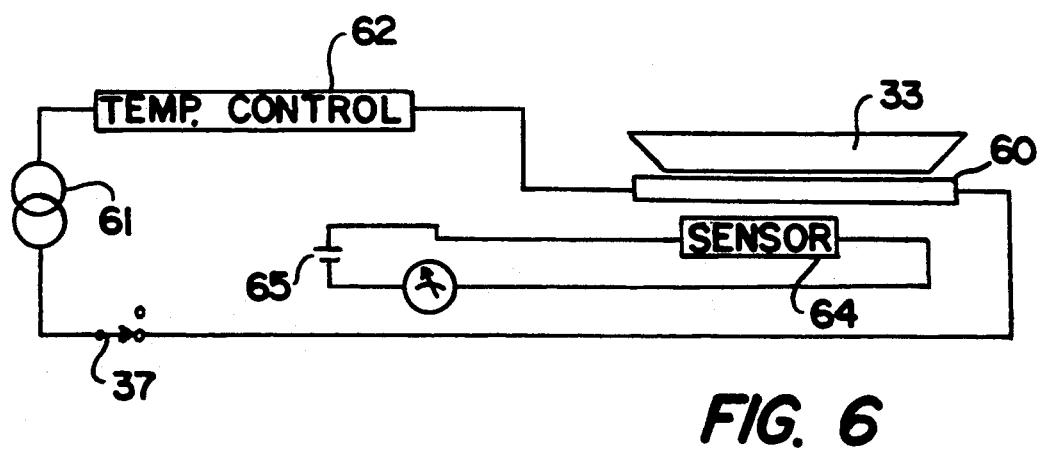
FIG. 6 is an electrical schematic diagram of the heating unit employed in the present invention.

The manner of heating sterile liquid in a heating basin (e.g., heating basin 33 of FIG. 3) is illustrated schematically in FIG. 6. Specifically, an electrical circuit includes a power source 61 connected in series with a temperature control unit 62, a heater element 60 and power control switch 37. Heater 60 is typically a thin wafer-like member disposed along the bottom surface of heating basin 33, secured to the basin by a suitable pressure sensitive adhesive having efficient heat transfer characteristics. Heater 60, may, for example, be of the type described in the aforementioned Templeton patent. Temperature control unit 62 includes a device for adjusting the current passing through the heating element 60 so as to permit selective adjustment of the heat applied to the liquid in basin 33. The power switch 37 permits selective application and removal of current flow with respect to the heater 60.

A temperature sensor 64 is disposed adjacent basin 33 to sense the temperature of the liquid therein. Sensor 64 is connected in series with a voltage source 65 and an indicator 66. Voltage source 65 and power source 61 may be the same source, or the voltage for one may be derived from the other. Indicator 66 measures the current through temperature sensor 64, that current being proportional to the sensed temperature. Indicator 66 and temperature controller 62 may correspond, for example, to the temperature controller/indicators 38 and 24 described above.

Figure 7:
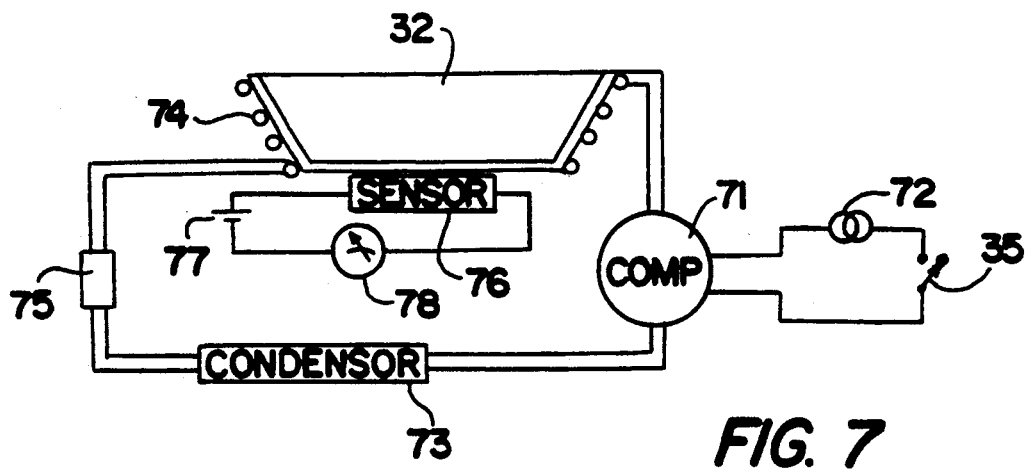
FIG. 7 is a schematic diagram of the cooling system employed in the present invention.

The refrigeration components illustrated schematically in FIG. 7 include a compressor 71 selectively actuable by means of an electrical power source 72 and an on-off power switch 35. Power source 72 may be the same source as power source 61, but separate power switches are provided for heating and cooling. The compressor 71 causes a suitable refrigerant fluid to flow through a series circuit including a condenser 73, an evaporator 74 and a suitable thermal expansion valve 75. The evaporator 74 is disposed about the sides of cooling basin 32 to permit cooling of the basin to a desired temperature. A temperature sensor 76 is disposed along the outside surface of the bottom of basin 32 to monitor the temperature of slush formed therein. Sensor 76 is connected in series with a voltage source 77, preferably derived from power source 72, and indicator 78. Indicator 78 measures the current passing through sensor 76 which, in turn, is proportional to the temperature sensed in basin 32.

From the foregoing description it will be appreciated that the invention makes available a novel method and apparatus for permitting surgical slush and warmed sterile liquid to be made available at a surgical procedure simultaneously.

Having described preferred embodiments of a new and improved method and apparatus for Method and Apparatus for Producing Surgical Slush and Heated Sterile Liquid in accordance with the present invention, is believed that other modifications, variations and changes will be suggested to persons skilled in the art after having access to the teachings set forth herein. It is therefore to be understood that all such variations, modifications and changes are believed to fall within the scope of the present invention as defined by the appended claims.

What is claimed is:

1. A method for providing sterile surgical slush comprising the steps of providing said sterile surgical slush in a selectively cooled cooling basin;

providing warmed sterile liquid in a selectively heated warming basin; and disposing said warming and cooling basins in close adjacency to provide simultaneous access to said sterile surgical slush and said warm sterile liquid.

2. The method of claim 1 further comprising the steps of:

covering said cooling and warming basins with a common sterile drape of material impervious to said surgical slush and to said sterile liquid; and contouring said drape to the configurations of said cooling and warming basins to provide respective drape receptacles in said basins for said surgical slush and said sterile liquid.

3. The method of claim 2 further comprising the step of disposing first and second centering indicia on said common drape, said centering indicia being spaced by the distance along said drape between the centers of said basins when said drape is contoured to fit in said basins.

4. The method of claim 2 further comprising the step of manually manipulating said drape to remove said surgical slush therefrom.

5. The method of claim 1 further comprising the step of selectively adding said slush from said cooling basin to the liquid in said warming basin.

6. The method of claim 1 further comprising the step of selectively adding warmed liquid from said warming basin to said surgical slush in said cooling basin.

7. The method of claim 1 further comprising the step of selectively and independently cooling said cooling basin and heating said warming basin.

* * * * *